(12) United States Patent
Mostafavi

(10) Patent No.: US 9,392,962 B2
(45) Date of Patent: Jul. 19, 2016

(54) PREDICTION OF BREATHING SIGNAL AND DETERMINING NON-PERIODICITY OF BREATHING USING SIGNAL-PHASE HISTOGRAM

(75) Inventor: Hassan Mostafavi, Los Altos, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 1283 days.

(21) Appl. No.: 13/078,903

(22) Filed: Apr. 1, 2011

(65) Prior Publication Data

US 2012/0253217 A1   Oct. 4, 2012

(51) Int. Cl.
*A61B 5/08*       (2006.01)
*A61B 5/11*       (2006.01)
*A61B 5/113*      (2006.01)
*A61B 6/02*       (2006.01)
*A61N 5/10*       (2006.01)
*A61B 5/00*       (2006.01)
*A61B 6/00*       (2006.01)

(Continued)

(52) U.S. Cl.
CPC .............. *A61B 5/08* (2013.01); *A61B 5/0816* (2013.01); *A61B 5/1128* (2013.01); *A61B 5/1135* (2013.01); *A61B 5/7292* (2013.01); *A61B 6/022* (2013.01); *A61B 6/5288* (2013.01); *A61N 5/1067* (2013.01); *A61B 5/0823* (2013.01); *A61B 5/7207* (2013.01); *A61B 6/032* (2013.01); *A61B 6/541* (2013.01); *A61N 2005/1059* (2013.01); *G06F 19/345* (2013.01); *G06F 19/3481* (2013.01)

(58) Field of Classification Search
CPC ............ A61B 5/08; A61B 5/11; A61B 5/113; A61B 5/1135; A61B 5/0816; A61B 5/0823; A61B 6/5288; A61B 6/541
USPC .................................................. 600/529–543
See application file for complete search history.

(56) References Cited

U.S. PATENT DOCUMENTS 4,930,508 A * 6/1990 Shimoni et al. ............... 600/410
5,505,199 A   4/1996 Kim
6,144,875 A   11/2000 Schweikard et al.
(Continued)

FOREIGN PATENT DOCUMENTS

CN       101035584 A   9/2007

OTHER PUBLICATIONS

Advisory Action dated Dec. 24, 2013, for U.S. Appl. No. 13/078,906.
(Continued)

*Primary Examiner* — Navin Natnithithadha
*Assistant Examiner* — Meredith Weare
(74) *Attorney, Agent, or Firm* — Vista IP Law Group, LLP; Gerald Chan; Peter Mei

(57) ABSTRACT

A method of processing breathing signals of a subject includes obtaining breathing signals of a subject, obtaining a signal-phase histogram using the breathing signals, wherein the signal-phase histogram comprises a plurality of data points, each of the data points having at least a phase value and a signal value, determining a reference value using at least some of the plurality of data points from the signal-phase histogram, determining whether a difference between the reference value and a signal value that is associated with a current respiratory cycle exceeds a threshold, and generating an output when the difference exceeds the threshold. A method of predicting breathing signal is also provided.

15 Claims, 10 Drawing Sheets

(51) Int. Cl.
　　*G06F 19/00*　　(2011.01)
　　*A61B 6/03*　　(2006.01)

(56) References Cited

U.S. PATENT DOCUMENTS

| 7,123,758 | B2 * | 10/2006 | Jeung et al. | 382/128 |
|---|---|---|---|---|
| 7,778,691 | B2 | 8/2010 | Zhang et al. | |
| 2003/0188757 | A1 | 10/2003 | Yanof et al. | |
| 2004/0071337 | A1 * | 4/2004 | Jeung et al. | 382/151 |
| 2004/0116804 | A1 * | 6/2004 | Mostafavi | 600/428 |
| 2005/0123183 | A1 * | 6/2005 | Schleyer et al. | 382/131 |
| 2005/0201510 | A1 * | 9/2005 | Mostafavi | 378/8 |
| 2008/0177280 | A1 | 7/2008 | Adler et al. | |
| 2008/0243018 | A1 * | 10/2008 | Zuhars et al. | 600/534 |
| 2010/0067739 | A1 * | 3/2010 | Mostafavi et al. | 382/103 |
| 2011/0009761 | A1 * | 1/2011 | Ruan et al. | 600/529 |

OTHER PUBLICATIONS

Non-final Office Action dated Feb. 6, 2014, for U.S. Appl. No. 13/078,906.
Final Office Action dated Sep. 10, 2013 for U.S. Appl. No. 13/078,906.
International Search Report and Written Opinion dated Jul. 27, 2012 for PCT/US2012/031766, 8 pages.
Non-final Office Action dated May 10, 2013 for U.S. Appl. No. 13/078,906.
Vedam et al. "Predicting Respiratory Motion for Four-Dimensional Radiotherapy", Med. Phys. vol. 31, Issue 8, pp. 2274-2283 (Aug. 2004).
Final Office Action dated May 19, 2014 for U.S. Appl. No. 13/078,906.
Advisory Action dated Aug. 1, 2014 for U.S. Appl. No. 13/078,906.
Non-final Office Action dated Sep. 12, 2014 for U.S. Appl. No. 13/078,906.
Merriam-Webster, "Processor", acquired Sep. 2014 url: http://www.merriam-webster.com/dictionary/processor.
Dictionary.Reference, "Processor", acquired Sep. 2014 url: http://dictionary.reference.com/browse/processor?r=66.
Extended European Search Report dated Aug. 4, 2014 for related EP Patent Application No. 12764756.8.
McCall et al., "Dual-Component model of respiratory motion based on the periodic autoregressive moving average (periodic ARM) method; Dual-component model of respiratory motion based on the periodic ARMA method" Physics in Medicine and Biology, Institute of Physics Publishing, Bristol GB, vol. 52, No. 12, Jun. 21, 2007, pp. 3455-3466, XP020112920.
Babovic et al., "Error correction of a predictive ocean wave model using local model approximation" Journal of Marine Systems, Elsevier, Amsterdam, NL, vol. 53, No. 1-4, Jan. 1, 2005, pp. 1-17, XP027807266.
Qing Ren et al., "Adaptive prediction of respiratory motion for motion compensation radiotherapy" Physics in Medicine and Biology, Institute of Physics Publishing, Bristol GB, vol. 52, No. 22, Nov. 21, 2007, pp. 6651-6661, XP020127250.
Notice of Allowance dated Aug. 6, 2015, for corresponding Chinese Patent Application No. 2012800221041, 4 pages.
Notice of Allowance and Fee(s) due dated Oct. 19, 2015 for related U.S. Appl. No. 13/078,906.
Notification of the First Office Action dated Jan. 4, 2015, for corresponding CN Patent Application No. 201280022104.1.
Final Office Action dated Feb. 25, 2015 for U.S. Appl. No. 13/078,906.
Advisory Action dated Jul. 8, 2015 for U.S. Appl. No. 13/078,906.

* cited by examiner

PREDICTION OF BREATHING SIGNAL AND DETERMINING NON-PERIODICITY OF BREATHING USING SIGNAL-PHASE HISTOGRAM

FIELD

This invention relates to systems and methods for processing breathing signals, and to systems and methods that use the results of the processing of breathing signals.

BACKGROUND

Radiation therapy has been employed to treat tumorous tissue. In radiation therapy, a high energy beam is applied from an external source towards the patient. The external source, which may be rotating (as in the case for arc therapy), produces a collimated beam of radiation that is directed into the patient to the target site. The dose and placement of the dose must be accurately controlled to ensure that the tumor receives sufficient radiation, and that damage to the surrounding healthy tissue is minimized.

Sometimes during a radiation therapy, the patient may be undergoing breathing motion. In such cases, it may be desirable to compensate for breathing motion during the treatment delivery session such that radiation may be properly delivered, or ceased to be delivered, to the target region. For example, if the patient's breathing becomes non-periodic (e.g., due to sudden movement such as coughing), then it may be desirable to stop a delivery of radiation. Compensating for breathing motion has two components: 1) determining the location of radiotherapy target, and 2) controlling component(s) of a radiation system, e.g., by turning the therapy beam on-off as in gating, redirecting the beam as in multi-leaf collimator (MLC) tracking, moving the patient support as in couch tracking, or a combination of the above.

There is a latency associated with current techniques of localizing the target. This is because current localization methods have a latency resulting from data acquisition and another latency resulting from the processing delays. There is also latency in the controlling of the components of a radiation system, such as mechanical motion required to either redirect the treatment beam or to reposition the patient. Applicant determines that in order to make the compensation for breathing motion temporally and geometrically accurate the overall latency from both the target localization and the controlling of machine components need to be overcome. In order to compensate for breathing motion, Applicant determines that it would be desirable to provide new techniques for predicting breathing signal, so that the overall latency from target localization and controlling of machine components can be overcome.

Also, unconstrained and normal breathing motion of a lung target is only approximately periodic and subject to variation in time. These changes can be a combination of baseline drift and breath-to-breath changes in amplitude and period in the order of 10 percent or more. More sudden changes caused by coughing or swallowing will result in even larger deviations from the normal breathing pattern. Sometimes, audio or visual coaching techniques can reduce these variations, but a 10 percent change is normal even after implementing these techniques in the clinic. Applicant of the subject application determines that there is a need to quantify the degree of non periodicity of breathing resulting from above variations, since it is expected to affect the performance of any prediction algorithm, and therefore the accuracy of determining the target position for management of motion. Also Applicant determines that it would be desirable to have a fast responding and prospective measure of non periodicity that can be used to interrupt the treatment beam when a sudden deviation from normal breathing pattern occurs. In order to compensate for deviation from periodicity (e.g., due to coughing), Applicant determines that it would be desirable to provide new techniques for determining non-periodicity.

Also, in current radiation therapy techniques, the internal target region is periodically imaged (e.g., using x-ray) to verify the position of the internal target region during a treatment session. Applicant determines that periodically imaging of internal target region is not desirable because it increases radiation dose delivered to the patient. Thus, Applicant also determines that it would be desirable to provide a technique for triggering imaging process that is non-periodic.

SUMMARY

In accordance with some embodiments, a method of processing breathing signals of a subject includes obtaining breathing signals of a subject, obtaining a signal-phase histogram using the breathing signals, wherein the signal-phase histogram comprises a plurality of data points, each of the data points having at least a phase value and a signal value, determining a reference value using at least some of the plurality of data points from the signal-phase histogram, determining whether a difference between the reference value and a signal value that is associated with a current respiratory cycle exceeds a threshold, and generating an output when the difference exceeds the threshold. In some embodiments, the signal value that is associated with a current respiratory cycle may be a signal value that is associated with a current time instant in the respiratory cycle.

In accordance with other embodiments, a system for processing breathing signals of a subject includes a processor configured for obtaining breathing signals of a subject, obtaining a signal-phase histogram using the breathing signals, wherein the signal-phase histogram comprises a plurality of data points, each of the data points having at least a phase value and a signal value, determining a reference value using at least some of the plurality of data points from the signal-phase histogram, determining whether a difference between the reference value and a signal value that is associated with a current respiratory cycle exceeds a threshold, and generating an output when the difference exceeds the threshold. In some embodiments, the signal value that is associated with a current respiratory cycle may be a signal value that is associated with a current time instant in the respiratory cycle.

In accordance with other embodiments, a computer product has a set of instructions stored in a non-transitory medium, wherein an execution of the instructions causes a process to be performed, the process comprising obtaining breathing signals of a subject, obtaining a signal-phase histogram using the breathing signals, wherein the signal-phase histogram comprises a plurality of data points, each of the data points having at least a phase value and a signal value, determining a reference value using at least some of the plurality of data points from the signal-phase histogram, determining whether a difference between the reference value and a signal value that is associated with a current respiratory cycle exceeds a threshold, and generating an output when the difference exceeds the threshold. In some embodiments, the signal value that is associated with a current respiratory cycle may be a signal value that is associated with a current time instant in the respiratory cycle.

In accordance with other embodiments, a method of processing breathing signals of a subject includes obtaining breathing signals of a subject, determining a signal-phase histogram using the breathing signals, wherein the signal-phase histogram comprises a plurality of data points, each of the data points having at least a phase value and a signal value, obtaining a current signal value that is associated with a current time instant in a respiratory cycle, obtaining a future phase value, and predicting a future signal value using the current signal value, the future phase value, and the signal-phase histogram.

In accordance with other embodiments, a system for processing breathing signals of a subject includes a processor configured for obtaining breathing signals of a subject, determining a signal-phase histogram using the breathing signals, wherein the signal-phase histogram comprises a plurality of data points, each of the data points having at least a phase value and a signal value, obtaining a current signal value that is associated with a current time instant in a respiratory cycle, obtaining a future phase value, and predicting a future signal value using the current signal value, the future phase value, and the signal-phase histogram.

In accordance with other embodiments, a computer product has a set of instructions stored in a non-transitory medium, wherein an execution of the instructions causes a process to be performed, the process comprising obtaining breathing signals of a subject, determining a signal-phase histogram using the breathing signals, wherein the signal-phase histogram comprises a plurality of data points, each of the data points having at least a phase value and a signal value, obtaining a current signal value that is associated with a current time instant in a respiratory cycle, obtaining a future phase value, and predicting a future signal value using the current signal value, the future phase value, and the signal-phase histogram.

Other and further aspects and features will be evident from reading the following detailed description of the embodiments, which are intended to illustrate, not limit, the invention.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

DESCRIPTION OF THE EMBODIMENTS

Figure 1:
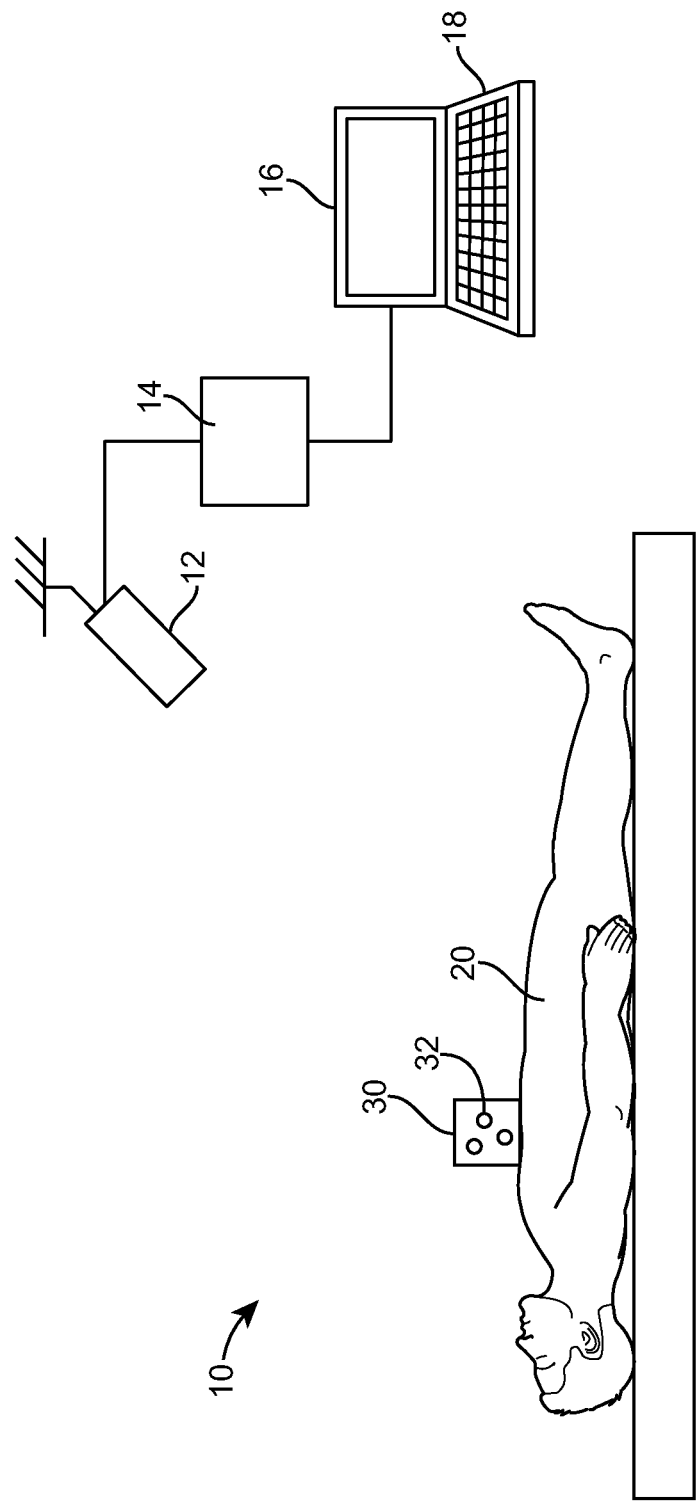
FIG. 1 illustrates a breathing monitoring system in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 illustrates a breathing monitoring system 10 in accordance with some embodiments. The breathing monitoring system 10 includes a camera 12, a processor 14 communicatively coupled to the camera 12, a monitor 16, and an input device 18. The camera 12 is oriented to view towards a patient 20. In the illustrated embodiments, a marker block 30 is placed on the patient 20, and the camera 12 is positioned so that it can view the marker block 30. The processor 14 is configured to process image signals (an example of breathing signals) from the camera 12, and process the image signals to thereby monitor the breathing of the patient 20. In some embodiments, the image signals and/or results of the processing of the image signals may be displayed on the monitor 16, for allowing a user to view them. Also, in some embodiments, the user may use the input device 18 to input parameters for processing of the image signals. In other embodiments, the monitor 16 and the input device 18 are not necessary, and the device 10 does not include components 16, 18.

As shown in the figure, the marker block 30 includes a plurality of markers 32 that are viewable by the camera 12. Each marker 32 may include a reflective material so that it can be more easily detected by the camera 12. In the illustrated embodiments, the relative positions among the markers 32 are predetermined. The processor 14 is configured to determine the position of the marker block 30 using the predetermined relative positions of the markers 32. In particular, the processor 14 is configured to compare the pattern of the markers 32 in the image provided by the camera 12 with known pattern of the markers 32 based on the predetermined relative positions of the markers 32. Based on the comparison, the processor 14 then determines the position of the marker block 30. By continuously processing image signals and determining the position of the marker block 30, the processor 14 can determine the breathing amplitude of the patient 20 in substantially real time.

Figure 2:
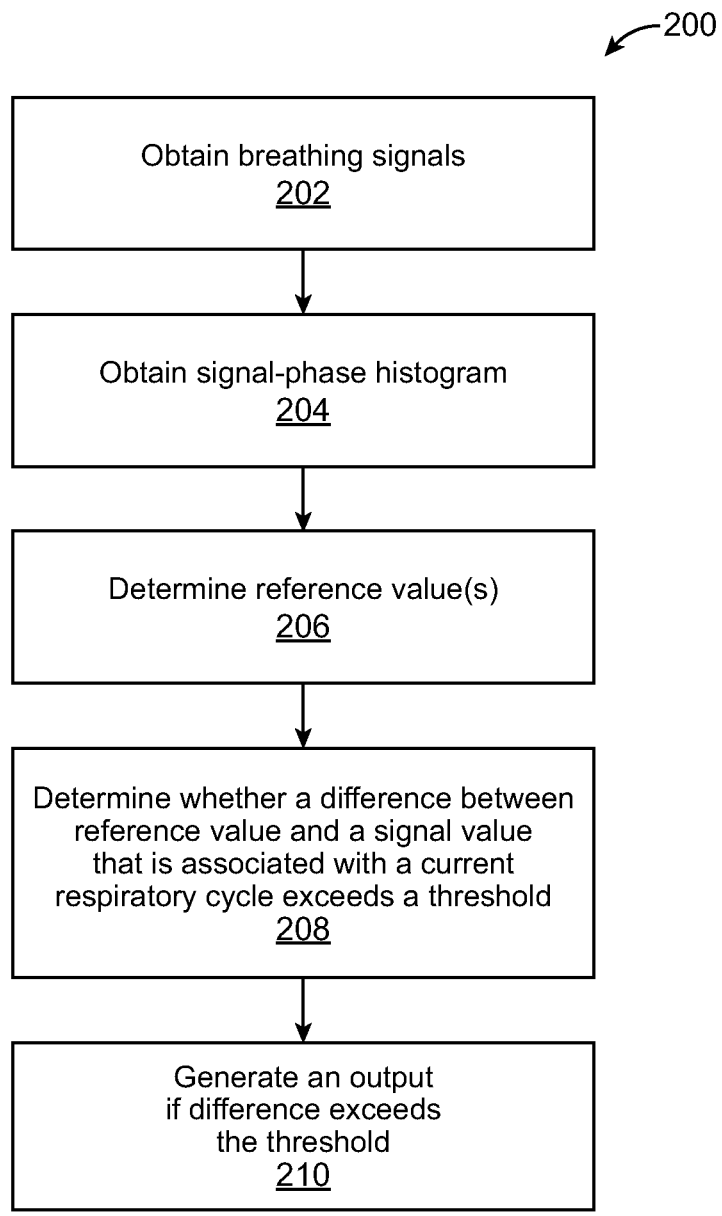
FIG. 2 illustrates a method of processing breathing signals to determine non-periodicity in breathing in accordance with some embodiments.

FIG. 2 illustrates a method 200 of processing breathing signals in accordance with some embodiments. In the illustrated embodiments, the method 200 is performed by the system 10 (e.g., processor 14) of FIG. 1. First, breathing signals of the patient are obtained (step 202). In some embodiments, such may be accomplished by the processor 14 receiving image signals from the camera 12, wherein the image signals themselves may be considered breathing signals. In other embodiments, image signals are processed by the processor 14 to determine breathing amplitudes. In such cases, the breathing amplitudes may be considered breathing signals, and the act of obtaining breathing signals may be accomplished by processing the image signals to determine breathing amplitudes using the processor 14. In other embodiments, instead of using the camera 12 (which does not involve any radiation) to obtain the image signals, the image signals may be obtained using a radiation source (e.g., x-ray, CT, etc.), or other imaging devices, such as MRI, ultrasound, etc. It should be noted that as used in this specification, the term "breathing signal" or similar term may refer to any information that may represent, or that may be used to determine, a breathing state or a breathing characteristic of a subject.

Figure 3:
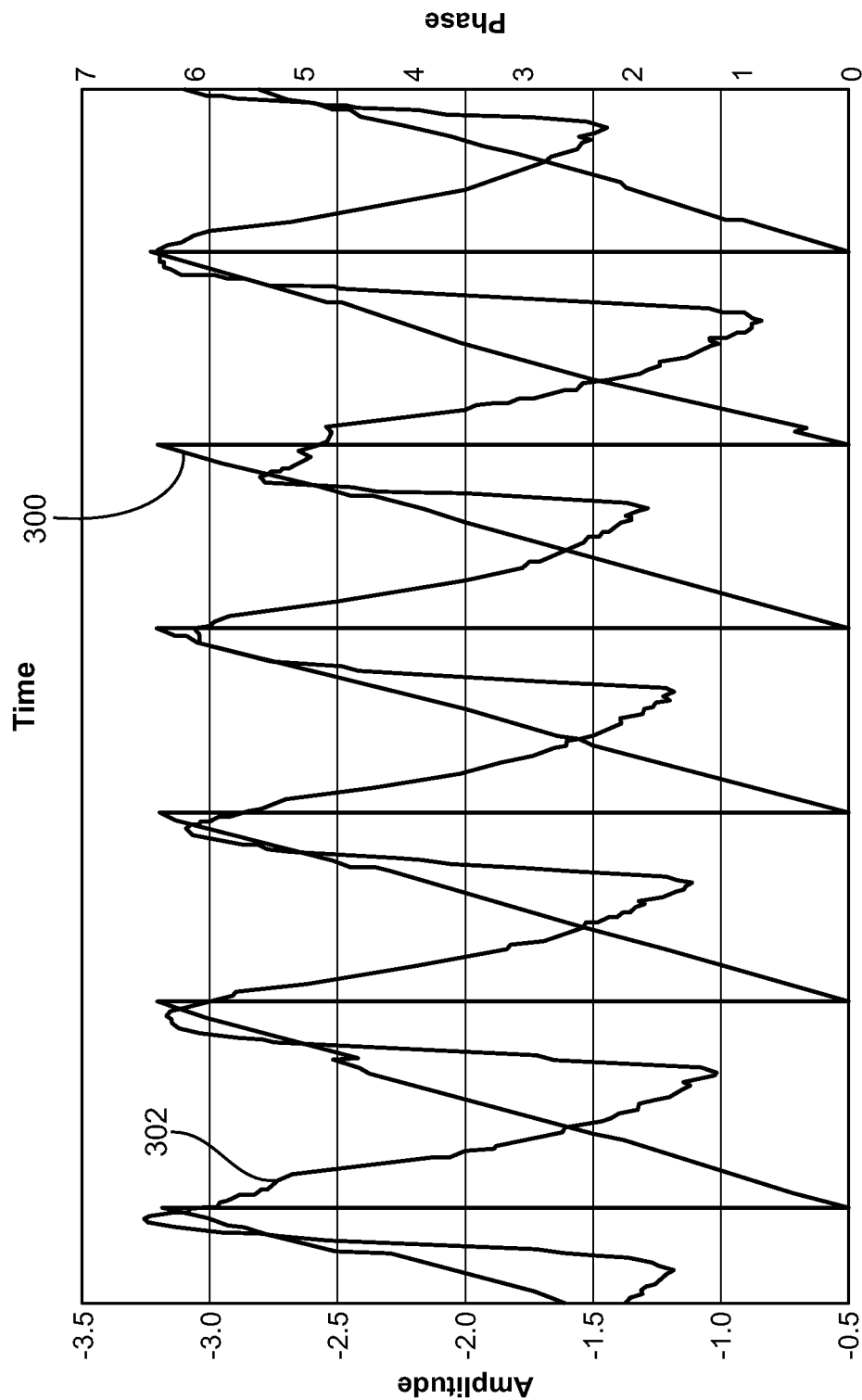
FIG. 3 is an exemplary chart showing phase and amplitude for a periodic signal.

Next, the processor 14 determines a signal-phase histogram using the breathing signals (step 204). In the illustrated embodiments, the signal-phase histogram includes a plurality of data points, with each of the data points having at least a phase value and a signal value. In one implementation, for each breathing amplitude (which may be a position of any bodily part that moves due to breathing, a position of an object coupled to such bodily part, or any signal that is associated with breathing), the processor 14 determines a corresponding breathing phase for the breathing amplitude. The phase of a physiological cycle represents a degree of completeness of a physiological cycle. In some embodiments, the phases of a respiratory cycle may be represented by a phase variable having values between 0° and 360°. FIG. 3 illustrates an example of a phase diagram 300 that is aligned with a corresponding amplitude/position diagram 302. Amplitude diagram 302 includes positional points of the marker block 30 determined using embodiments of the technique described herein. Each point in the amplitude diagram 302 represents a position of the marker block 30 or a bodily part at a certain point in time. In the illustrated example, a phase value of 0° (and 360°) represents a peak of an inhale state, and the phase value varies linearly between 0° and 360° in a physiological cycle. As shown in the diagram, for each point in the amplitude diagram 302 at certain point in time, a corresponding phase value at the same point in time may be obtained. Thus, for each breathing amplitude, the processor 14 can determine the corresponding phase of the respiratory cycle. In some embodiments, the determined phase may be considered an example of a breathing signal. In such cases, the act of determining the phase by the processor 14 may be performed in step 202 to obtain the breathing signal.

Figure 4:
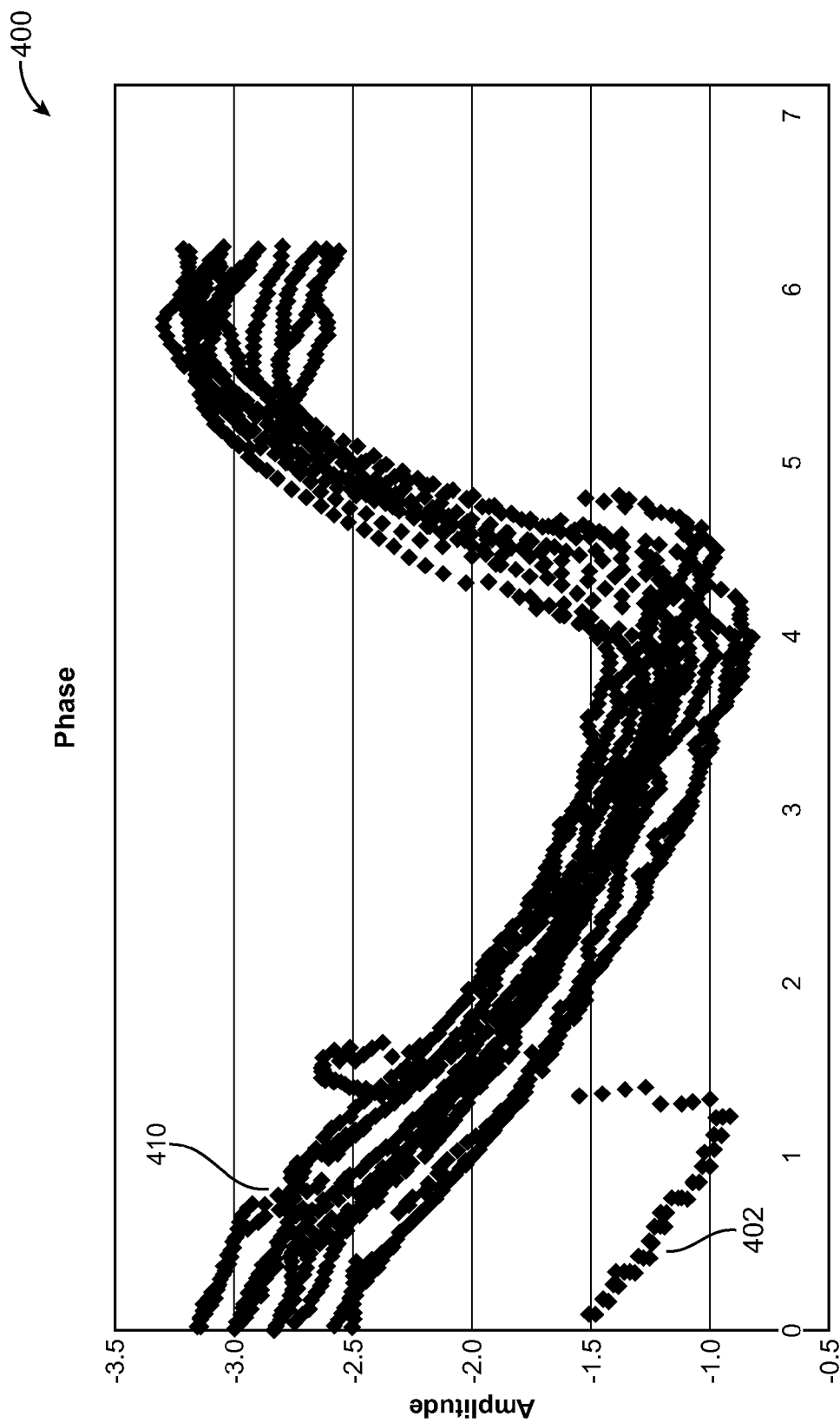
FIG. 4 illustrates an example of a signal-phase histogram.

In the illustrated embodiments, as the patient 20 is undergoing breathing, the processor 14 continues to determine data points (signal, phase), with the signal representing a breathing amplitude. The data points are collected over time using the system 10, and are then used to generate the signal-phase histogram. FIG. 4 illustrates an example of a signal-phase histogram 400 that is generated using the above technique. In the example of the signal-phase histogram 400, the x-axis represents phase values ranging from 0 to $2\pi$, and the y-axis represents amplitude (or signal) values. In other embodiments, the x-axis may represent amplitude (or signal) values, and the y-axis may represent phase values. In one technique, the histogram 400 is implemented as an array having a 64-times-64 array of bins covering the range of phase values (from 0 to $2\pi$) in the horizontal dimension, and the range of respiration signal amplitudes in the vertical dimension. The amplitude and phase of each new sample are used to increment the corresponding bin in histogram array 400. In other embodiments, the array may have different sizes. For example, in other embodiments, the array may have a 128-times-128 array of bins.

In some embodiments, the processor 14 is configured to update the histogram 400 by disregarding data points that are older than a prescribed period. In some cases, the prescribed period may be determined by a user, and input into the processor 14 using the input device 18. For example, a user interface may be provided in the screen 16 that allows the user to enter a time (t), or a number of breathing cycles (N), each of which may be considered an example of a prescribed period. For each data point on the histogram 400 that is determined by the processor 14, the processor 14 also time stamps the data point—e.g., by assigning a time value or a breathing cycle number, to identify when the data point was determined. During the breathing monitoring process, the processor 14 is configured to decrement the bins in the histogram 400 having data points that are older than the prescribed period. For example, if a data point at a bin is time stamped with a breathing cycle number of "2," and the current breathing cycle is at "6," and assuming that the prescribed period is 4 cycles (meaning that the histogram 400 will not include data points that are older than 4 cycles), then the processor 14 will update the bin by decrementing a count value to disregard the data point because the data point is for a breathing cycle that occurred more than 4 cycles ago. In the illustrated embodiments, the prescribed period may be selected by a user, and may be input by the user. The above technique prevents the processor 14 from determining that there is non-periodicity in the breathing due to slow variation in the breathing pattern, thereby allowing slow variation in the patient's breathing during the breathing monitoring process.

Returning to the method 200 of FIG. 2, next, the processor 14 determines reference value(s) using at least some of the plurality of data points from the signal-phase histogram (step 206). In some embodiments, a reference value may be determined by obtaining an average of the signal values for a given phase value in the histogram array 400. For example, if phase bin that corresponds to phase value of P or phase range P1-P2 has signal values of S1, S2, and S3, then the reference value may be determined as the average of these three signal values. In other embodiments, the number of count in each bin of the histogram array 400 may be used to determine a weighted average, which weighted average is then used as the reference value. In the above example, if signal value S3 has three counts, and S1 and S2 each has one count in the bin of the histogram array 400, then signal value S3 may be given more weight in determining the weighted average. In the above embodiments, the reference values for the respective phase bins of the histogram 400 are average values. In other embodiments, the reference values may be median values (e.g., weighted median values) for the respective phase bins in the histogram 400.

In other embodiments, the average or median of signal values for the current phase is calculated only over the prior breathing cycles, and the current signal value is not used in calculating the average or the median. For example, in one implementation, the average or median is calculated before the current signal-phase bin in the histogram is incremented. This technique allows deviation from previous cycles to be determined.

In other embodiments, the determined reference values in the histogram 400 may optionally be used to determine a reference curve that best fit through and/or among the reference values. For example, in the embodiments in which the reference values are average values, the best fit curve represents the average values for different respective phase values.

In the embodiments in which the reference values are median values, the best fit curve then represents the median values for different respective phase values.

Next, the processor 14 determines whether a difference between the reference value and a signal value that is associated with a current respiratory cycle exceeds a threshold (step 208). The threshold is predetermined (e.g., it may be arbitrarily set by a user of the system 10), and may be input by the user using the input device 18. In other embodiments, the threshold may be preprogrammed into the processor 18.

Figure 5:
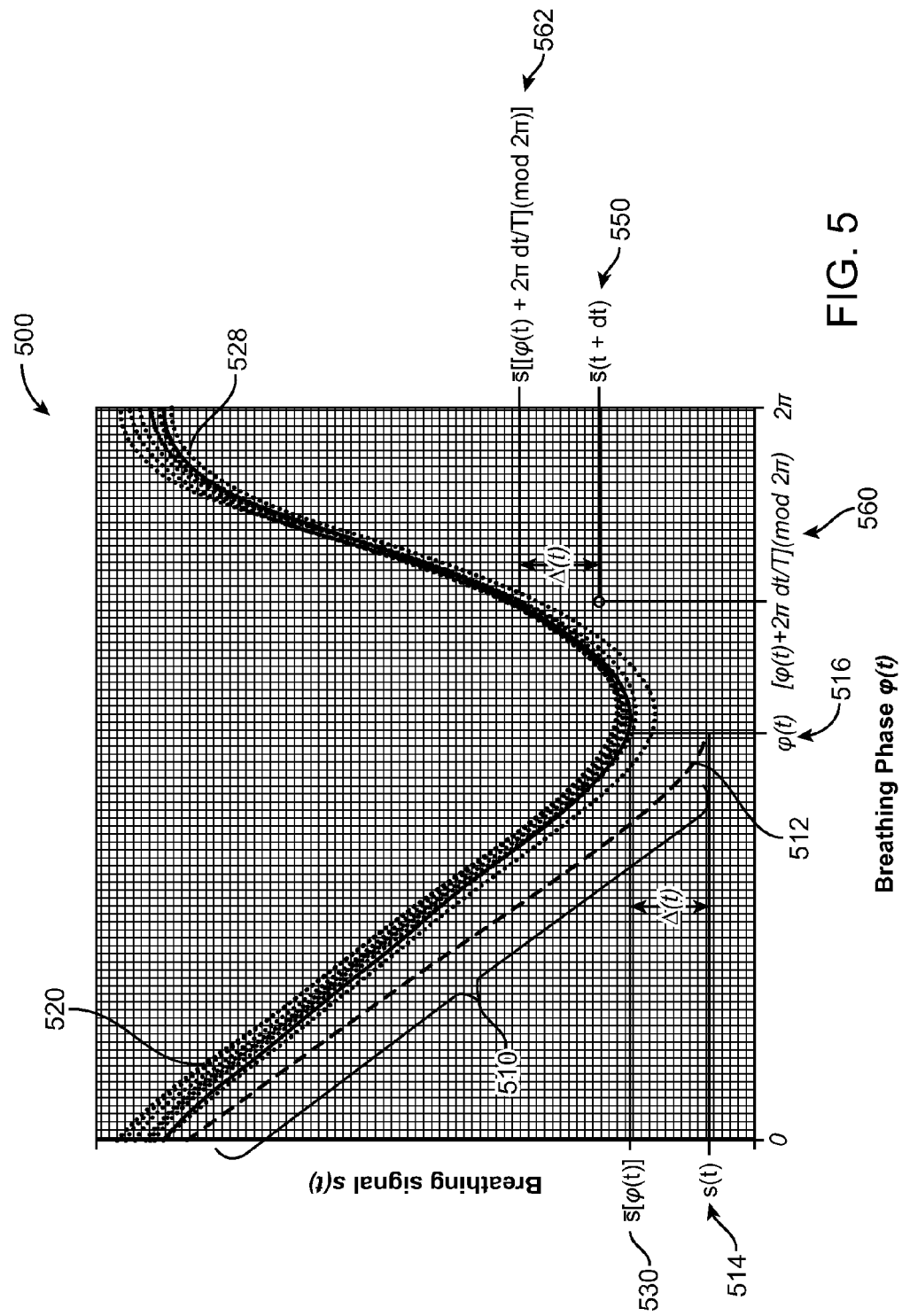
FIG. 5 illustrates a concept of determining reference value(s) in a signal-phase histogram.

One implementation of the action 208 is illustrated in the example of FIG. 5. As shown in the figure, data points 510 represented by the dashed line are from the current respiratory cycle, with data points 512 being the latest data point that has been obtained (e.g., data point at the current time instant). Data points 520 in the histogram 500 are from the previous respiratory cycles. The histogram 500 also has a solid line 528 representing reference values for different respective phase values that are determined in step 206. The latest data point 512 used to update the histogram 500 has signal value 514 and an associated phase (or phase bin) value 516. In the illustrated example, for the phase value 516 that is associated with the latest signal 514, the histogram 500 has a corresponding reference signal value 530 that is determined from step 206. In step 208, the processor 14 compares the signal 514 with the reference signal value 530 (e.g., by determining the difference $\Delta(t)$ between the two).

In the illustrated embodiments, if the difference $\Delta(t)$ between the reference value 530 and the signal value 514 exceeds the threshold, the processor 14 then generates an output (e.g., a signal) (step 210), indicating that there is non-periodicity in the patient's breathing. For example, the processor 14 may generate an output to activate an audio device to cause the audio device to emit an audio signal. In another example, the processor 14 may generate an output to cause information be displayed on the monitor 16. In other embodiments, the processor 14 may generate an output to use and/or control a device, such as a treatment radiation machine, or an imaging device.

In the above embodiments, deviation $\Delta(t)$ of the latest signal value 514 from average or median 530 over past cycles at the corresponding latest phase 516 is used to determine non-periodicity (e.g., it is used as the value of non-periodicity). In particular, the deviation $\Delta(t)$ from the latest data point in the recent history is used without change as the measure of a deviation from periodicity. In such technique, the processor 14 does not extrapolate the deviation based on the recent history of deviations.

In other embodiments, instead of using $\Delta(t)$ from the latest data point without change, the processor 14 is configured to extrapolate the deviation based on the recent history of the deviations. In such cases, the processor 14 is configured to analyze the data points in the recent history, and use the pattern of deviations to extrapolate the deviation. For example, the processor 14 may use linear extrapolation to determine the deviation. In this embodiment of prediction, the extrapolated value can be used as the value of non-periodicity. In other embodiments, instead of linear extrapolation, other degrees of extrapolation may be used.

It should be noted that the measure of non-periodicity (whether forward extrapolation from recent history is used or not) is "prospective" because there is no need to wait and retrospectively see how well the prediction works in order to get a measure on periodicity.

In some embodiments, the difference signal $\Delta(t)$ (the difference between the current signal sample and the prior cycles cluster average) for determining the measure of non-periodicity may also be used to estimate a breathing signal. In some cases, it may be useful to predict a breathing signal in a future time in order to compensate for any latency that may exist in a radiation system. For example, in some embodiments, if it is desirable to deliver radiation (e.g., treatment radiation or imaging radiation) when the subject is at breathing state X, and assuming that it may take a radiation system a duration of P to activate the various components to deliver the radiation beam, then it may be useful to predict the breathing state at least P ahead of time so that the latency of the radiation system may be compensated. This is beneficial because this may allow the radiation beam to be delivered precisely at the appropriate time when the subject is at breathing state X.

The concept of predicting the signal value at a forward time is illustrated in FIG. 5. In the figure, the future breathing signal 550 is predicted for a future phase 560 by taking the difference ($\Delta(t)$) between the latest signal 514 and the reference value 530, and applying the same difference for the future phase 560. In particular, the same difference is added to the reference value 562 at the future phase 560 to obtain the predicted future breathing signal 550. It should be noted that how much the phase value needs to be forwarded (i.e., the phase difference between value 560 and value 516) depends on how much latency needs to be compensated, i.e., how much forward prediction is needed. In some embodiments, the amount of forward phase may be entered as an input to the processor 14 by a user. For a given latency time P that needs to be compensated, the corresponding phase difference (P/T*360°) can be determined by the processor 14. In other embodiments, instead of using $\Delta(t)$ from the latest data point without change for predicting the breathing signal, the processor 14 is configured to extrapolate the deviation based on the recent history of the deviations (as similarly discussed with reference to determining measure of non-periodicity) for predicting the breathing signal. In such cases, the extrapolated value is added to the reference value 562 at the future phase 560 to obtain the predicted future breathing signal 550.

The mathematical concepts of determining value of non-periodicity, and prediction of breathing signal, in accordance with some embodiments is now further discussed with reference to FIG. 5. As discussed, the processor 14 is configured to estimate the phase of the breathing cycle $\phi(t)$ from the breathing signal s(t) in real time where $\phi(t)$ goes from 0 at end-inhale to $2\pi$ at the following end-inhale. The signal-phase histogram is formed by accumulating the sample pairs $[\phi(t),s(t)]$ in a two-dimensional (2D) histogram array. Refer back to FIG. 5, which shows a graphical representation of the signal-phase histogram. The processor 14 first learns the breathing pattern from the signal-phase clustering of data samples over 3 to 4 initial breathing cycles. Subsequently, the processor 14 produces a continuous and real-time measure of non periodicity of breathing. FIG. 5 shows how the pattern of clustering of signal-phase samples in the 2D histogram is used to see how far a new sample is from the past history of the signal at any given time.

In FIG. 5, the dashed line trace shows the breathing signal during the ongoing breathing cycle where the latest signal-phase sample $[\phi(t),s(t)]$ is used to increment the corresponding histogram bin. The signal samples for each phase $\phi$ is averaged over prior breathing cycles and forms the cluster average function $\bar{s}(\phi)$, $[\phi \epsilon (0.2\pi)]$. This function defines the average or median breathing pattern up to the latest data point. Note that since $\bar{s}(\phi)$ is a function of phase rather than time, it allows for variations of breathing period T which may be estimated by the processor 14 in some embodiments. The estimate of T is updated at every newly detected end-inhale and end-exhale point of the breathing cycle.

For the purpose of predicting the breathing signal at a future time (e.g., future relative to the latest data point), the processor 14 is configured to extrapolate the breathing signal forward while conforming to the shape of the average/median breathing pattern defined by the function $\bar{s}(\phi)$. For this, the processor 14 uses the current estimate of period T to transform the forward time (t+τ) to the forward phase [φ(t)+2πτ/T](mod 2π). In some embodiments, the difference signal Δ(t) ≜ s(t)−$\bar{s}$[φ(t)] may be defined as the difference between the current signal sample and the prior cycles cluster average. In order to obtain the forward predicted signal value ŝ(t+τ), the processor 14 extrapolates Δ(t) forward in time and then add it to the prior cluster average at the forward phase [φ(t)+2πτ/T] (mod 2π):

$$\hat{s}(t+\tau)=\bar{s}[[(\phi(t)+2\pi\tau/T)](\mathrm{mod}\ 2\pi)]+\hat{\Delta}(t+\tau)$$

where $\hat{\Delta}(t+\tau)$ is the forward extrapolation of Δ(t), and $\bar{s}$[[φ(t)+2πτ/T](mod 2π)] is the prior cluster average at the forward phase [φ(t)=2πτ/T](mod 2π). The forward extrapolation of Δ(t) can be a zero-order extrapolation where $\hat{\Delta}(t+\tau)$= Δ(t) or it can be higher order such as linear extrapolation using most recent samples of Δ(t) over a short period, e.g., 0.5 Sec.

In some embodiments, the real-time signal defining the measure of non periodicity is defined as the absolute value of $\hat{\Delta}(t+\tau)$ that is the forward extrapolated difference between signal and the prior cluster average $N_T(t) \triangleq |\hat{\Delta}(t+\tau)|$.

The non periodicity function $N_T(t)$ is a real-time signal parallel to the breathing signal s(t) which can be used prospectively as an indication of breathing behavior at time (t+τ). As such, it can be used to trigger a prescribed action, such as beam-hold or image acquisition, in response to irregular breathing. It should be noted that for zero-order extrapolation of the deviations, the difference function $N_\tau(t)$ does not depend on τ, but for linear and higher order extrapolation, it depends on the length of forward prediction time.

As discussed above with reference to the method 200 of FIG. 2, non-periodicity of breathing may be quantified (measured) in the form of a secondary signal derived in real time from the breathing signal. The instantaneous prediction error associated with the above prediction technique is the difference between s(t), the actual signal at time t, and the signal ŝ(t) predicted τ seconds earlier. This can be retrospectively defined as $e_\tau(t) \triangleq s(t)-\hat{s}(t)$. One possible measure of prediction error is defined as the root mean square (RMS) value of this difference $$E(\tau, W) \triangleq \sqrt{\frac{1}{n_W} \sum_{t \in W} |e_\tau(t)|^2}$$

It is calculated over a specified time window w of $n_w$ samples that can for example be the length of a treatment session. It has been determined that the method 200 of FIG. 2 provides a high correlation between non-periodicity measure and prediction error for different forward times that range from 200 mSec to at least 700 mSec. Also, using the method 200 of FIG. 2 for different forward times, it has been determined that the prediction errors correlate well with different respective forward times.

In some embodiments, embodiments of the above technique for predicting signal value yields a prediction error of 1.75 mm (e.g., difference between actual position/amplitude and predicted position/amplitude) or less for 350 mSec of forward extrapolation time, and yields a prediction error of 2.5 mm or less for 500 mSec of forward extrapolation time, wherein the prediction errors are expressed in terms of amplitude (or position) that is associated with the patient's breathing. In some embodiments, the forward time may be an input to the algorithm. The forward time can be anything from very small, even zero, to over several seconds. The prediction error increases with forward time, but compared to existing techniques, it increases relatively less. For example, a forward prediction time of 200 mSec may be sufficient to overcome the latency associated with target localization and the latency associated with the controlling of component(s) in some radiation machines. In other cases, the forward extrapolation time (e.g., how far in the future the target position needs to be predicted) may be other values, depending on the technique of target localization, the component(s) of the radiation machine and imaging systems that needs to be controlled, and their respective latencies that need to be overcome.

In the above embodiments, the camera 14 has been described as being configured to view the marker block 30. In other embodiments, the marker block 30 is not necessary, in which case, the camera 14 may be used to view the patient 20. For examples, the camera 14 may be used to view the body of the patient 20, the clothes of the patient 20, and/or a blanket that is covering the patient 20. In these embodiments, the processor 14 is configured to perform image processing to identify landmark(s) in the images to thereby determine breathing information (e.g., breathing amplitudes, breathing phase, etc.) for the patient 20.

In the above embodiments, the system 10 is described as having a camera 12 for obtaining image signals that can be used to determine breathing amplitudes. In other embodiments, the system 10 may not include the camera 12. Instead, the system 10 may include other types of devices for providing breathing information. For example, in other embodiments, the system 10 may include a strain-gauge that is coupled to the patient 20. In such cases, the strain-gauge is communicatively coupled to the processor 14 for providing signals that represent breathing amplitudes of the patient 20. In other embodiments, the system 10 may include a sensor coupled to the patient's mouth and/or nose for sensing the breathing of the patient 20. The processor 14 is communicatively coupled to the sensor, and receives signals from the sensor. The signals may represent the breathing amplitudes, or may be used to obtain breathing amplitudes and/or breathing phases. In some embodiments, the breathing signal includes the position coordinates of internal anatomy landmarks, the tumor, and/or implanted fiducials. These position coordinates may be measured by various methods, including X-ray imaging, MRI, or other types of imaging. In further embodiments, internal target tracking may be employed that uses radio frequency transponder(s) implanted in or near the target region (e.g., tumor). The transponder(s) is localized by an external array antenna transmitting query signals and processing the transponder response signals. Other types of breathing sensing devices may be used with the processor 14 in other embodiments.

Figure 6:
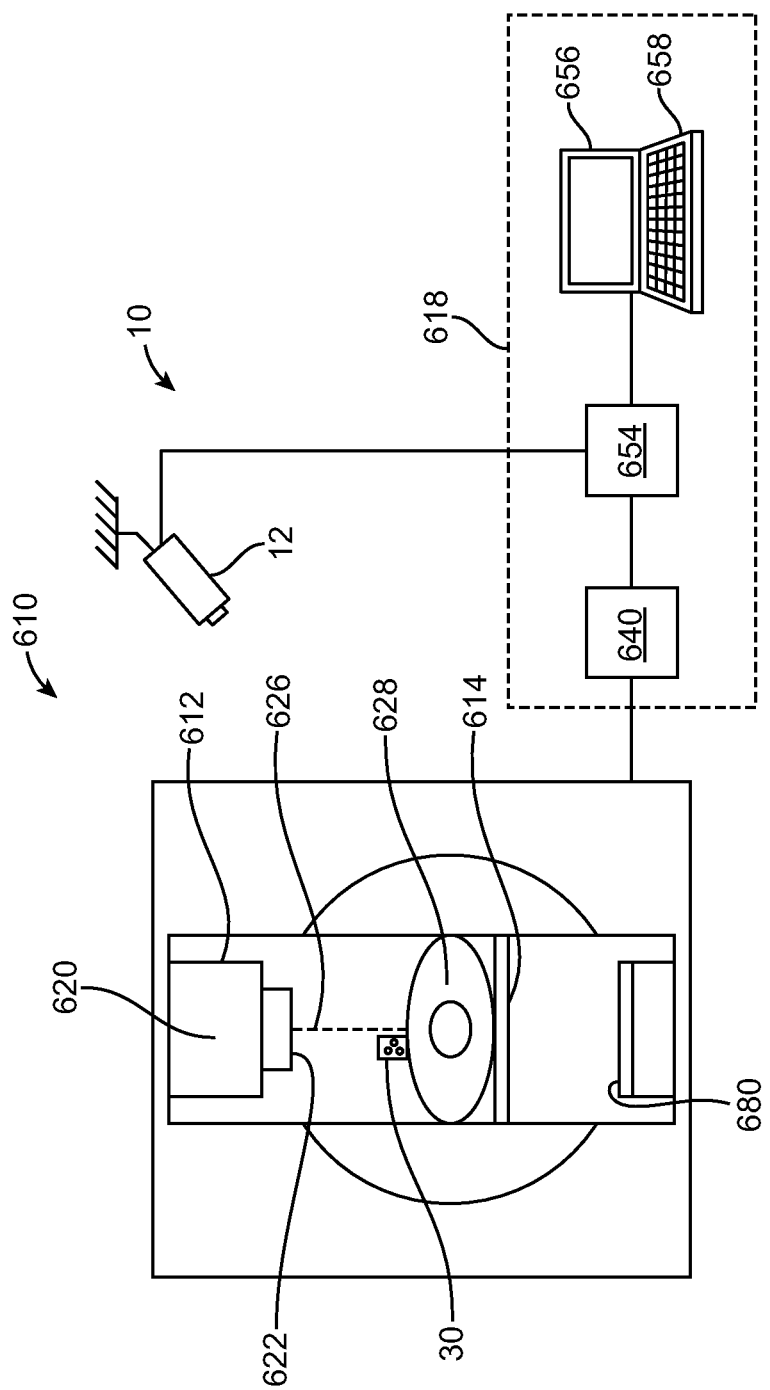
FIG. 6 illustrates a radiation system that uses the breathing monitoring system of FIG. 1 in accordance with some embodiments.

The breathing monitoring system 10 and the method 200 described previously may be used with a variety of medical devices, and in various different medical procedures. In some embodiments, the breathing monitoring system 10 may be used with a treatment radiation machine. FIG. 6 illustrates a radiation system 610 that is used with the breathing monitoring system 10. The system 610 is a treatment system that includes a gantry 612, a patient support 614 for supporting a patient, and a control system 618 for controlling an operation of the gantry 612. The gantry 612 is in a form of an arm. The system 610 also includes a radiation source 620 that projects a beam 626 of radiation towards a patient 628 while the patient 628 is supported on support 614, and a collimator system 622 for controlling a delivery of the radiation beam 626. The radiation source 620 can be configured to generate a cone beam, a fan beam, or other types of radiation beams in different embodiments.

In the illustrated embodiments, the radiation source 620 is a treatment radiation source for providing treatment energy. In other embodiments, in addition to being a treatment radiation source, the radiation source 620 can also be a diagnostic radiation source for providing diagnostic energy for imaging purpose. In such cases, the system 610 will include an imager, such as the imager 680, located at an operative position relative to the source 620 (e.g., under the support 614). In further embodiments, the radiation source 620 may be a treatment radiation source for providing treatment energy, wherein the treatment energy may be used to obtain images. In such cases, in order to obtain imaging using treatment energies, the imager 680 is configured to generate images in response to radiation having treatment energies (e.g., MV imager). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 620 is able to generate X-ray radiation at a plurality of photon energy levels within a range anywhere between approximately 10 keV and approximately 20 MeV. In further embodiments, the radiation source 620 can be a diagnostic radiation source. In the illustrated embodiments, the radiation source 620 is coupled to the arm gantry 612. Alternatively, the radiation source 620 may be located within a bore.

In the illustrated embodiments, the control system 618 includes a processor 654, such as a computer processor, coupled to a control 640. The control system 618 may also include a monitor 656 for displaying data and an input device 658, such as a keyboard or a mouse, for inputting data. The operation of the radiation source 620 and the gantry 612 are controlled by the control 640, which provides power and timing signals to the radiation source 620, and controls a rotational speed and position of the gantry 612, based on signals received from the processor 654. Although the control 640 is shown as a separate component from the gantry 612 and the processor 654, in alternative embodiments, the control 640 can be a part of the gantry 612 or the processor 654. The processor 654 may be the processor 14, or may include features implemented in the processor 14 of the breathing monitoring system 10. In such cases, the radiation system 610 and the breathing monitoring system 10 share the same processor or parts of a same processor. Alternatively, the processor 654 may be a different processor from the processor 14.

In some embodiments, when using the system 610 of FIG. 6, the radiation source 620 is rotated about the patient 628 to deliver treatment radiation from a plurality of gantry angles, for example, as in arc therapy. As treatment radiation is being delivered to the patient 628, the breathing monitoring system 10 of FIG. 1 may be used to monitor the breathing of the patient 628. In some embodiments, the processor 654 processes the signals from the camera 12 to determine breathing amplitudes of the patient 628, and then gates the delivery of the treatment radiation based on the amplitudes. For example, the processor 654 may cause the radiation source 620 to deliver radiation, or to stop a delivery of radiation, when the determined amplitude is within a prescribed amplitude range.

In other embodiments, the processor 654 processes the signals from the camera to determine respiratory phases of the patient 628, and then gates the delivery of the treatment radiation based on the respiratory phases. For example, the processor 654 may cause the radiation source 620 to deliver radiation, or to stop a delivery of radiation, when the determined phase is within a prescribed phase range. In further embodiments, the processor 654 processes the signals from the camera 12 to detect non-periodicity, and then gates the delivery of the treatment radiation based on the detection of non-periodicity. In other embodiments, instead of, or in addition to, controlling the delivery of radiation, the processor 654 may be configured to control the gantry 612 (e.g., stop, accelerate, or decelerate the gantry 612), and/or to position the patient support 614, based on the determined amplitude and/or phase, or detection of non-periodicity.

During the treatment process, the processor 654 monitors the patient's 628 breathing, and correlates feature(s) of the breathing (such as breathing signals, breathing amplitudes, breathing phases, etc.) with positions of internal target region that is being irradiated by the radiation beam 626. For example, based on images received from the camera 12, the processor 654 then determines the phase/amplitude of the breathing cycle. The phase of the breathing cycle or the amplitude is then used by the processor 654 to determine a position of the internal target region based on a pre-established relationship between breathing phase/amplitude and position of internal target region. In some embodiments, the relationship between the breathing phase/amplitude and target position may be pre-determined by a physician during a treatment planning process. For example, during a treatment planning process, it may be determined that when a patient is at breathing phase=40°, the corresponding position of the internal target region is at position X=45 mm, Y=23 mm, and Z=6 mm relative to the isocenter. This technique allows the treatment radiation system 610 to target delivery of radiation towards the target region based on breathing signals obtained by the system 10. Thus, it has the benefit of obviating the need to continuously or periodically imaging the internal target region using X-ray imaging, which may be harmful to the patient due to its additional radiation dose.

In one method of using the system 10 with the radiation system 610, the processor 654 is configured to detect non-periodicity in the patient's 628 breathing using the technique described with reference to FIGS. 2-5. When the processor 654 determines that there is non-periodicity in the patient's 628 breathing, the processor 654 may generate a signal (e.g., a beam-stop signal) to cause the radiation source 620 to stop delivering radiation, and/or a signal to control a motion of the gantry 612 (e.g., to stop the gantry, decelerate the gantry 612, or accelerate the gantry 612). By using the above described technique to quantify the non-periodicity in the form of a secondary signal derived in real time from the breathing signal, the system 10 provides a fast responding and prospective measure of non-periodicity that can be used to interrupt the treatment beam when a sudden deviation from normal breathing pattern occurs. In particular, because the instantaneous value of the measure of non-periodicity is a fast acting prospective indication of any deviation from normal breathing, the system 10 allows interventions, such as radiotherapy beam-hold, that can be triggered in time.

As discussed, the external optical tracking surrogate signal (e.g., camera signal) represents the anterior-posterior (AP) displacement of the chest or abdomen with patient in supine position. The forward predicted value of this one-dimensional signal, along with the internal-external correlation model, is used by the processor 654 to predict the internal 3D position of the target. Using the camera signal as a surrogate signal to measure internal target position is advantageous, because it allows the three-dimensional position of the internal target at a future time to be predicted (estimated) rapidly. In particular, because the camera signal is a one-dimensional signal that can be obtained and processed quickly, and because the camera provides a high sample rate, it provides almost no latency (at least when compared to latency associated with the controlling of the component(s) of the radiation system 610). However, in other embodiments, the surrogate signal needs not be a camera signal, and may be other types of signal, as discussed, which may also have a high sample rate.

Figure 7:
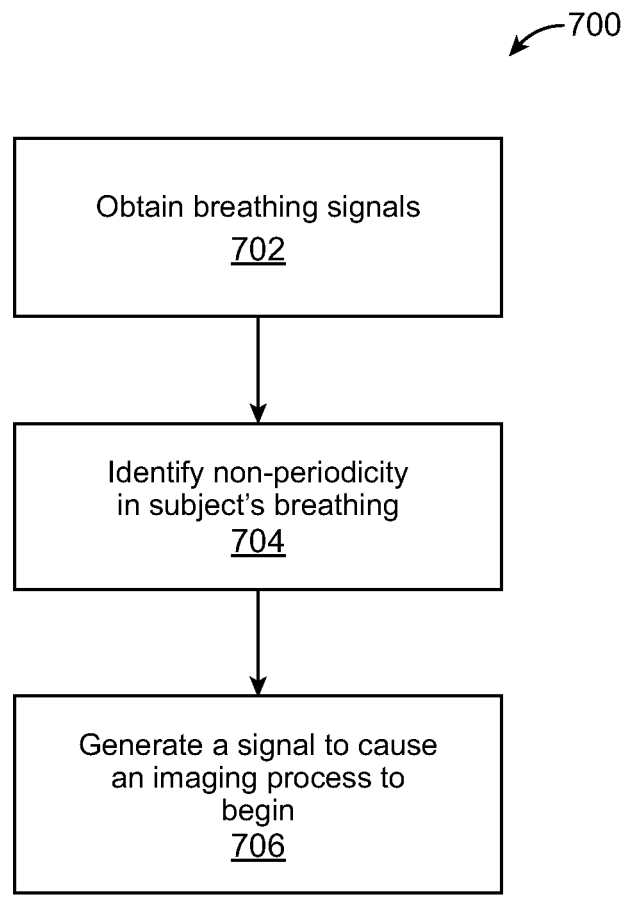
FIG. 7 illustrates a method of triggering an imaging procedure in accordance with some embodiments.

In other embodiments, as an alternative, or in addition, to controlling component(s) of the radiation system 610, if the radiation system 610 has imaging capability, the processor 654 may be configured to generate a signal to trigger an imaging process to image the internal target region when the processor 654 determines that there is non-periodicity in the patient's 628 breathing. FIG. 7 illustrates a method 700 of triggering an imaging process in accordance with some embodiments. In the method 700, the processor 654 obtains breathing signals (step 702), and the processor 654 then analyzes the breathing signals to identify a non-periodicity in a subject's breathing (step 704). Embodiments of performing the steps 702, 704 are similar to those described previously with reference to the method 200.

When the processor 654 determines that there is non-periodicity in the patient's 628 breathing, the processor 654 then generates a signal to cause an image process to begin (706). In the illustrated embodiments, if the radiation system 610 has imaging capability (e.g., if the radiation system 610 has the imager 680), the image process may be performed by the system 610. For example, the radiation source 620 may deliver imaging radiation having diagnostic energy (e.g., in kv range), or radiation having treatment energy level (e.g., in MeV range) to generate one or more images of the internal region using the imager 680. Alternatively, a separate imaging system may be used to generate the image(s) of the internal region. For example, the separate imaging system may be a CT system, an x-ray system, an ultrasound imaging device, a MRI system, a tomosynthesis imaging system, a PET system, a SPECT system, or any other system that is capable of obtaining an image of the internal target region.

In some embodiments, the image(s) of the internal target region is used by the processor 654 to verify the position of the target region, and/or to confirm the pre-established relationship between breathing feature (amplitude, phase, etc.) and target position. In other embodiments, the image of the internal target region may also be used by the processor 654 to verify the relationship between breathing feature and target position (e.g., external-internal correlation model). If a result of the verification process indicates that the model is inaccurate, the processor 654 may update (e.g., modify, recreate, etc.) the relationship between breathing feature and target position (e.g., external-internal correlation model), so that the updated relationship may be used by the system 610 to deliver additional radiation to the patient 628 (e.g., to control the radiation source, collimator, gantry, and/or patient support). In other embodiments, the processor 654 may cause the radiation process to stop if the result of the verification process indicates that the model is inaccurate.

In other embodiments, the image(s) of the internal target region determined from the method 700 may be used by the processor 654 to determine the position of the internal target region using stereo imaging technique. In stereo imaging technique, a set of reference images are first obtained. The reference images may be obtained before the treatment process begins. Each of the reference images is obtained when the internal target region is at a certain position, and therefore, each reference image is associated with a certain position of the target region. In some embodiments, the reference images may be generated using a CT system by rotating the radiation source of the CT system at different gantry angles while the target is undergoing motion. Thus, the reference images are obtained at different times. In other embodiments, if the system 610 has imaging capability, the reference images may be generated using the system 610. In some embodiments, after the image (input image) from the method 700 is obtained, the processor 654 then selects one or more reference images from the reference image set that spatially correspond with the input image. In one technique, the processor 654 determines a projection line that extends between the source that generates the input image and the target image in the image frame. The processor 654 also determines a plurality of projection lines for respective reference images, wherein each projection line extends between the source and the target image in the corresponding reference image. The processor 654 then determines, for each projection line, an epipolar distance that is between the projection line of the input image and the projection line for the corresponding reference image. The epipolar distance is measured in a direction that is perpendicular to both the projection line of the input image and the projection line of the reference image. In some embodiments, the processor 654 is configured to select a reference image that spatially corresponds with the input image by comparing the epipolar distances with a prescribed threshold. If the epipolar distance for a reference image is below the prescribed threshold, then it may be determined that the target's position when the input image is generated (during method 700) corresponds (e.g., is the same relative to certain arbitrary coordinate system) with the target's position when the reference image is generated. In such cases, the processor 654 then selects such reference image for determining the position of the target region. In some embodiments, the position of the midpoint at the epipolar line between the projection line of the input image and the projection line of the selected reference image may be used as the position of the target. Stereo imaging technique has been described in U.S. patent application Ser. No. 12/211,686, filed on Sep. 16, 2008, the entire disclosure of which is expressly incorporated by reference herein.

It should be noted that using detected non-periodicity of patient's breathing to trigger an imaging of internal region is advantageous because it obviates the need to periodically image the internal region for verification of the position of the internal region and for verification of the relationship between breathing and target positions. Periodic imaging of internal region is not desirable because it complicates the treatment procedure. Also, in the case in which radiation is used to image internal region, periodic imaging using radiation is also not desirable because it increases the radiation dosage to the patient 628.

Figure 8:
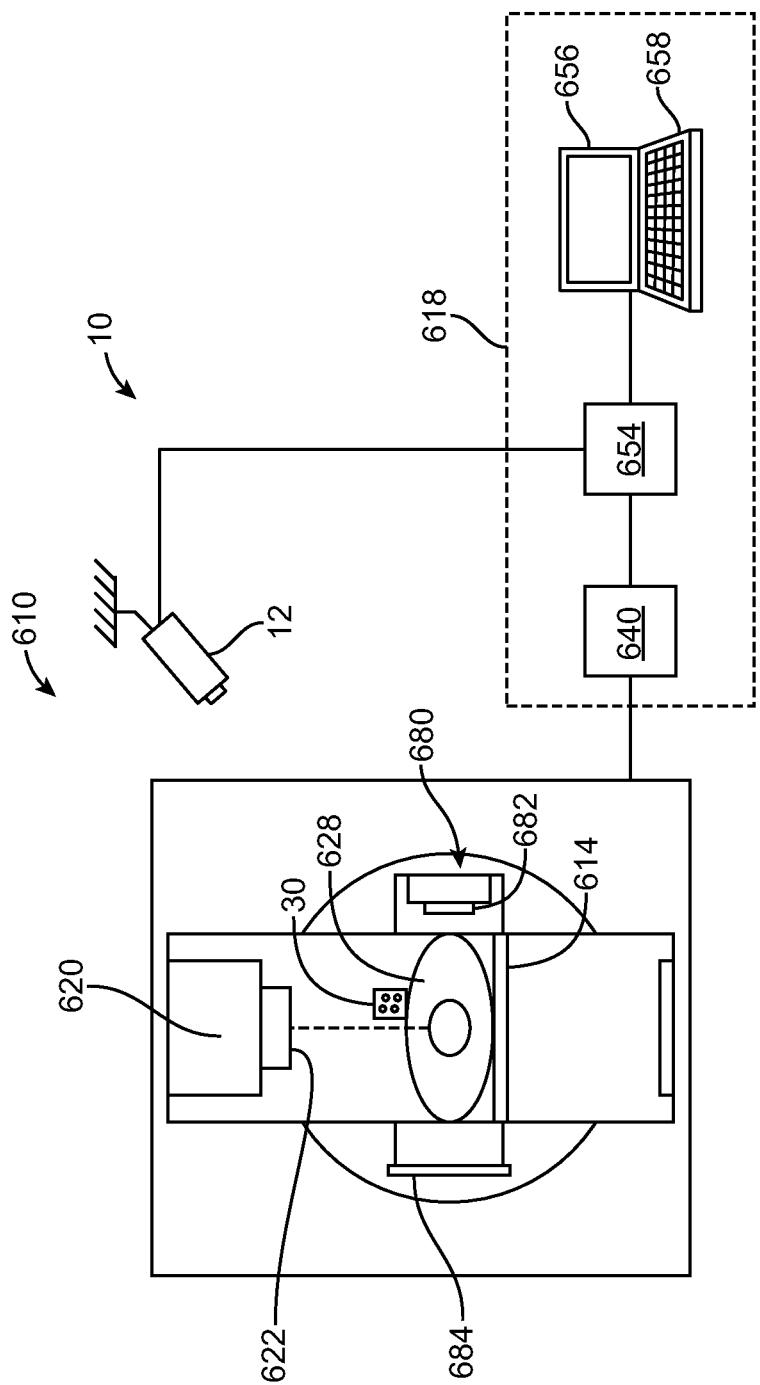
FIG. 8 illustrates another radiation system that uses the breathing monitoring system of FIG. 1 in accordance with other embodiments.

As discussed, in other embodiments, the system 610 may include an additional imaging device. FIG. 8 illustrates a variation of the system 610 that further includes an additional imaging device 680 in accordance with some embodiments. In the illustrated embodiments, the imaging device 680 includes a diagnostic radiation source 682 and an imager 684 opposite from it. In the illustrated embodiments, the radiation source 620 is configured to provide treatment radiation, and the diagnostic radiation source 682 is configured for generating image(s) using low energy beam (e.g., kV imaging system). The radiation sources 620, 682 are integrated into a same gantry 612 (e.g., oriented relative to each other at 90°), or alternatively, may be separate devices that are placed adjacent to each other, and may be rotated at different speeds. In other embodiments, instead of coupling the radiation sources 620, 682 to the arm gantry 612, the radiation sources 620, 682 may be coupled to a common ring gantry, or to different respective ring gantries that can be rotated together or relative to each other. The method of using the system of FIG. 8 is similar to that described previously with reference to FIG. 6.

Figure 9:
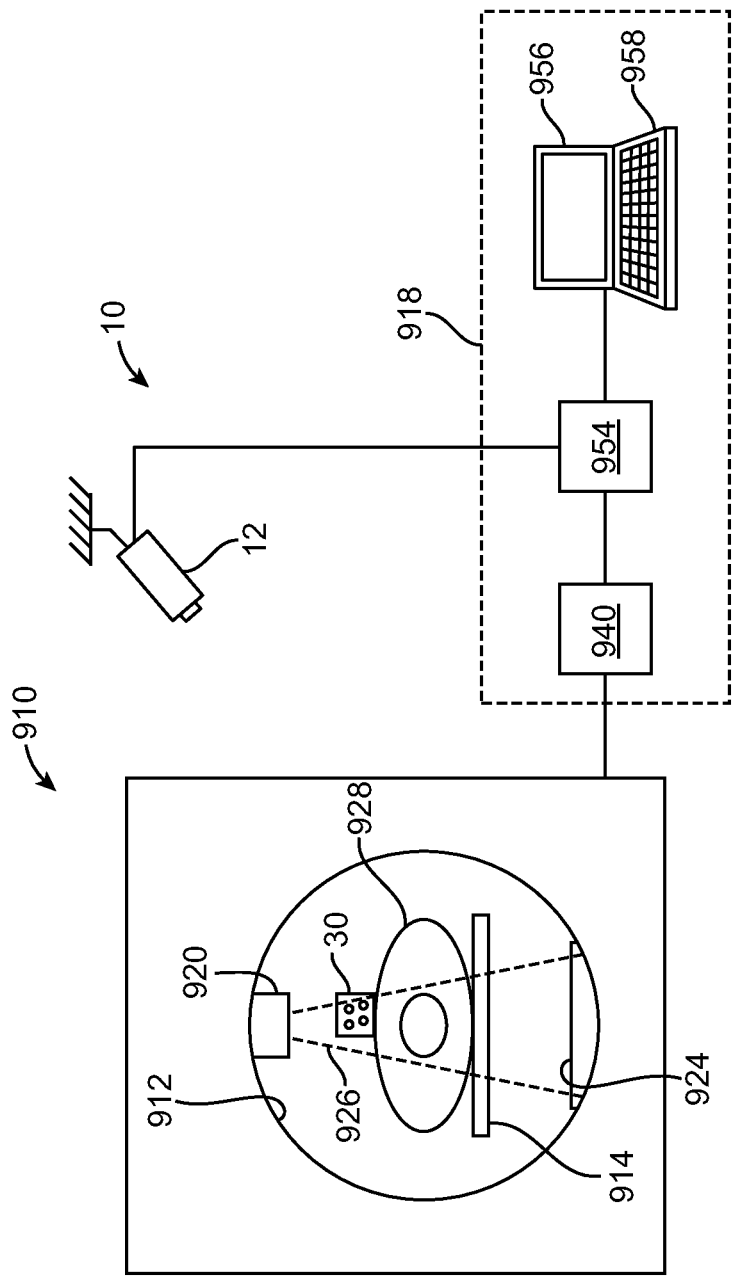
FIG. 9 illustrates another radiation system that uses the breathing monitoring system of FIG. 1 in accordance with other embodiments.

In further embodiments, instead of using the breathing monitoring system 10 with a device that has treatment capability, the breathing monitoring system 10 may be used with an imaging device. FIG. 9 illustrates a computed tomography system 910 that is used with the breathing monitoring system 10 in accordance with some embodiments. The system 910 includes a gantry 912, and a support 914 for supporting a patient 928. The gantry 912 includes an x-ray source 920 that projects a beam 926 of x-rays towards a detector 924 on an opposite side of the gantry 912 while the patient 928 is positioned at least partially between the x-ray source 920 and the detector 924. By means of non-limiting examples, the beam of x-rays can be a cone beam or a fan beam. The detector 924 has a plurality of sensor elements configured for sensing a x-ray that passes through the patient 928. Each sensor element generates an electrical signal representative of an intensity of the x-ray beam as it passes through the patient 928.

The system 910 also includes a control system 918. In the illustrated embodiments, the control system 918 includes a processor 954, such as a computer processor, coupled to a control 940. The control system 918 may also include a monitor 956 for displaying data and an input device 958, such as a keyboard or a mouse, for inputting data. The operation of the radiation source 920 and the gantry 912 are controlled by the control 940, which provides power and timing signals to the radiation source 920, and controls a rotational speed and position of the gantry 912, based on signals received from the processor 954. Although the control 940 is shown as a separate component from the gantry 912 and the processor 954, in alternative embodiments, the control 940 can be a part of the gantry 912 or the processor 954. The processor 954 may be the processor 14, or may include features implemented in the processor 14 of the breathing monitoring system 10. In such cases, the radiation system 910 and the breathing monitoring system 10 share the same processor or parts of a same processor. Alternatively, the processor 954 may be a different processor from the processor 14.

It should be noted that the system 910 is not limited to the configuration described above, and that the system 910 may have other configurations in other embodiments. For example, in other embodiments, the system 910 may have a different shape. In other embodiments, the radiation source 920 of the system 910 may have different ranges of motions and/or degrees of freedom. For example, in other embodiments, the radiation source 920 may be rotatable about the patient 928 completely through a 360° range, or partially through a range that is less than 360°. Also, in other embodiments, the radiation source 920 is translatable relative to the patient 928. Further, the radiation source 920 is not limited to delivering diagnostic energy in the form of x-ray, and may deliver treatment energy for treating a patient.

During a scan to acquire x-ray projection data (i.e., CT image data), the gantry 912 rotates about the patient 928 at different gantry angles, so that the radiation source 920 and the imager 924 may be used to obtain images at different gantry angles. As the system 910 is operated to obtain images at different gantry angles, the patient 928 is breathing. Thus, the resulting images at different gantry angles may correspond to different phases of a breathing cycle for the patient 928. After the scan is completed, the projection images at different gantry angles are stored, e.g., in a memory (such as a non-transitory medium), and the projection images are processed to sort the images so that images at different gantry angles that correspond to a same phase of a breathing cycle are binned (e.g., associated with each other). The binned images for a specific phase of a respiratory cycle can then be used to generate a reconstructed three-dimensional CT image for that phase.

In some embodiments, when using the system 910 of FIG. 9, the radiation source 920 is rotated about the patient 928 to deliver diagnostic (imaging) radiation from a plurality of gantry angles. As radiation is being delivered to the patient 928, the breathing monitoring system 10 of FIG. 1 may be used to monitor the breathing of the patient 928. In some embodiments, the processor 954 processes the signals from the camera to determine breathing amplitudes of the patient 928, and then gates the delivery of the imaging radiation based on the amplitudes. For example, the processor 954 may cause the radiation source 920 to deliver radiation, or to stop a delivery of radiation, when the determined amplitude is within a prescribed amplitude range. In other embodiments, the processor 954 processes the signals from the camera to determine respiratory phases of the patient 928, and then gates the delivery of the radiation based on the respiratory phases. For example, the processor 954 may cause the radiation source 920 to deliver radiation, or to stop a delivery of radiation, when the determined phase is within a prescribed phase range. In other embodiments, instead of, or in addition to, controlling the delivery of radiation, the processor 954 may be configured to control the gantry 912 (e.g., stop, accelerate, or decelerate the gantry 912), and/or to position the patient support 914, based on the determined amplitude and/or phase.

In other embodiments of a method of using the system 10 with the radiation system 610, the processor 954 is configured to detect non-periodicity in the patient's 928 breathing using the technique described with reference to FIG. 2. When the processor 954 determines that there is non-periodicity in the patient's 928 breathing, the processor 954 may generate a signal (e.g., a beam-stop signal) to cause the radiation source 920 to stop delivering radiation, a signal to control a motion of the gantry 912 (e.g., to stop the gantry, decelerate the gantry 912, or accelerate the gantry 912), and/or a signal to position the patient support 914.

Computer System Architecture

Figure 10:
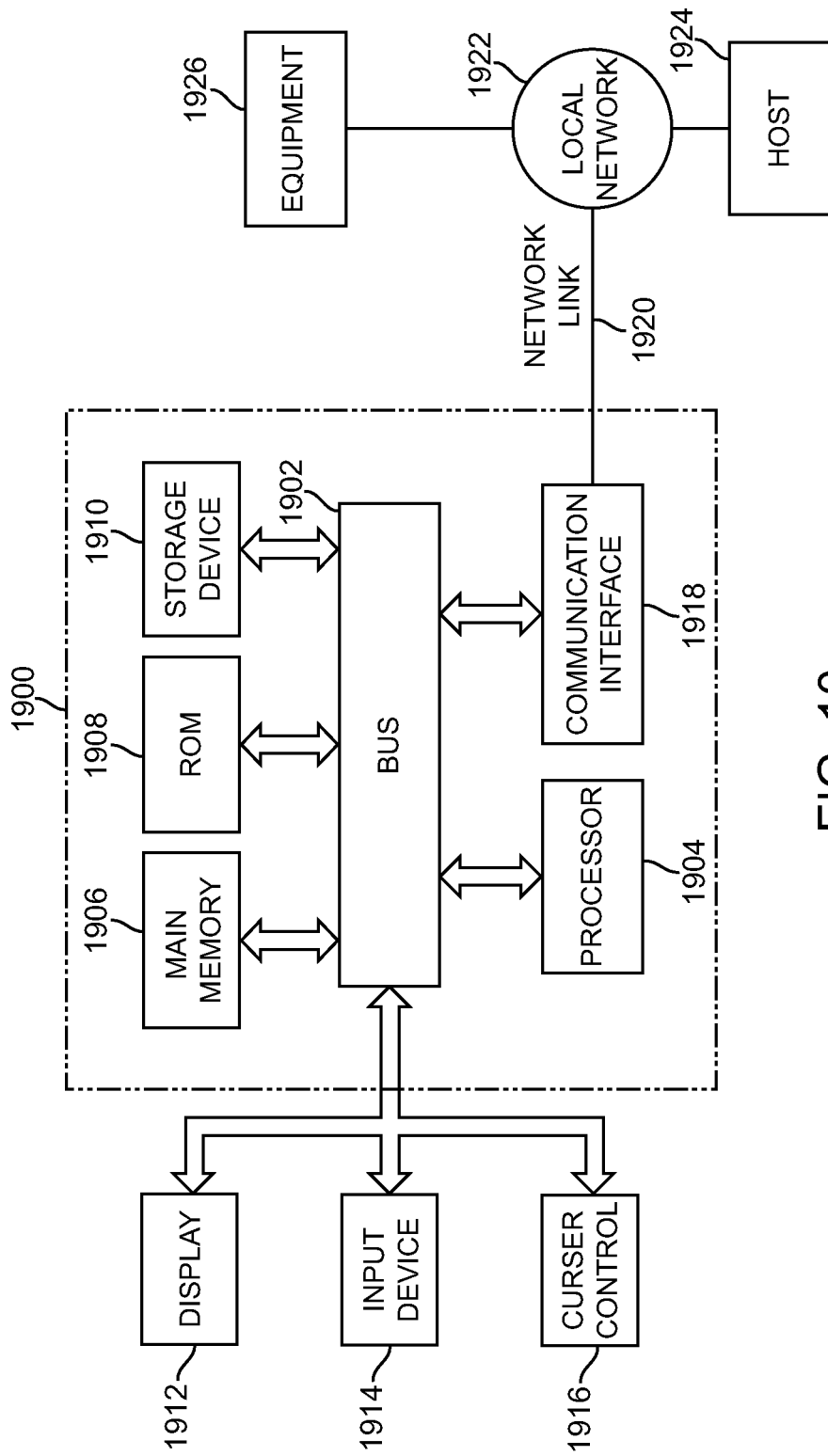
FIG. 10 is a block diagram of a computer system architecture, with which embodiments described herein may be implemented.

FIG. 10 is a block diagram that illustrates an embodiment of a computer system 1900 upon which an embodiment of the invention may be implemented. Computer system 1900 includes a bus 1902 or other communication mechanism for communicating information, and a processor 1904 coupled with the bus 1902 for processing information. The processor 1904 may be an example of the processor 14 of FIG. 1, or another processor that is used to perform various functions described herein. In some cases, the computer system 1900 may be used to implement the processor 14 (or other processors described herein). The computer system 1900 also includes a main memory 1906, such as a random access memory (RAM) or other dynamic storage device, coupled to the bus 1902 for storing information and instructions to be executed by the processor 1904. The main memory 1906 also may be used for storing temporary variables or other intermediate information during execution of instructions to be executed by the processor 1904. The computer system 1900 further includes a read only memory (ROM) 1908 or other static storage device coupled to the bus 1902 for storing static information and instructions for the processor 1904. A data storage device 1910, such as a magnetic disk or optical disk, is provided and coupled to the bus 1902 for storing information and instructions.

The computer system 1900 may be coupled via the bus 1902 to a display 1912, such as a cathode ray tube (CRT) or a flat panel, for displaying information to a user. An input device 1914, including alphanumeric and other keys, is coupled to the bus 1902 for communicating information and command selections to processor 1904. Another type of user input device is cursor control 1916, such as a mouse, a trackball, or cursor direction keys for communicating direction information and command selections to processor 1904 and for controlling cursor movement on display 1912. This input device typically has two degrees of freedom in two axes, a first axis (e.g., x) and a second axis (e.g., y), that allows the device to specify positions in a plane.

The computer system 1900 may be used for performing various functions (e.g., calculation) in accordance with the embodiments described herein. According to one embodiment, such use is provided by computer system 1900 in response to processor 1904 executing one or more sequences of one or more instructions contained in the main memory 1906. Such instructions may be read into the main memory 1906 from another computer-readable medium, such as storage device 1910. Execution of the sequences of instructions contained in the main memory 1906 causes the processor 1904 to perform the process steps described herein. One or more processors in a multi-processing arrangement may also be employed to execute the sequences of instructions contained in the main memory 1906. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 1904 for execution. Such a medium may take many forms, including but not limited to, non-volatile media, volatile media, and transmission media. Non-volatile media includes, for example, optical or magnetic disks, such as the storage device 1910. A non-volatile medium may be considered as an example of a non-transitory medium. Volatile media includes dynamic memory, such as the main memory 1906. A volatile medium may be considered as another exampler of a non-transitory medium. Transmission media includes coaxial cables, copper wire and fiber optics, including the wires that comprise the bus 1902. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1904 for execution. For example, the instructions may initially be carried on a magnetic disk of a remote computer. The remote computer can load the instructions into its dynamic memory and send the instructions over a telephone line using a modem. A modem local to the computer system 1900 can receive the data on the telephone line and use an infrared transmitter to convert the data to an infrared signal. An infrared detector coupled to the bus 1902 can receive the data carried in the infrared signal and place the data on the bus 1902. The bus 1902 carries the data to the main memory 1906, from which the processor 1904 retrieves and executes the instructions. The instructions received by the main memory 1906 may optionally be stored on the storage device 1910 either before or after execution by the processor 1904.

The computer system 1900 also includes a communication interface 1918 coupled to the bus 1902. The communication interface 1918 provides a two-way data communication coupling to a network link 1920 that is connected to a local network 1922. For example, the communication interface 1918 may be an integrated services digital network (ISDN) card or a modem to provide a data communication connection to a corresponding type of telephone line. As another example, the communication interface 1918 may be a local area network (LAN) card to provide a data communication connection to a compatible LAN. Wireless links may also be implemented. In any such implementation, the communication interface 1918 sends and receives electrical, electromagnetic or optical signals that carry data streams representing various types of information.

The network link 1920 typically provides data communication through one or more networks to other devices. For example, the network link 1920 may provide a connection through local network 1922 to a host computer 1924 or to equipment 1926 such as a radiation beam source or a switch operatively coupled to a radiation beam source. The data streams transported over the network link 1920 can comprise electrical, electromagnetic or optical signals. The signals through the various networks and the signals on the network link 1920 and through the communication interface 1918, which carry data to and from the computer system 1900, are exemplary forms of carrier waves transporting the information. The computer system 1900 can send messages and receive data, including program code, through the network(s), the network link 1920, and the communication interface 1918.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. For example, the term "image" needs not be limited to an image that is displayed visually, and may refer to image data that is stored. Also, the term "processor" may include one or more processing units, and may refer to any device that is capable of performing mathematical computation implemented using hardware and/or software. The term "processor" may also refer to software stored in a non-transitory medium in other embodiments. Further, in any of the embodiments described herein, instead of using the processor 14/654/954 to perform the various functions described, a separate processor may be used. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A method of processing breathing signals of a subject, comprising:
   obtaining breathing signals of a subject using a breathing monitoring device;

obtaining a signal-phase histogram using the breathing signals, wherein the signal-phase histogram comprises a plurality of data points, each of the data points having at least a phase value and a signal value;

determining, by a processing unit, a first reference value using at least some of the plurality of data points from the signal-phase histogram;

determining, by the processing unit, a difference between the first reference value and a signal value that is associated with a current respiratory cycle;

predicting, by the processing unit, a future signal value by:
determining, by the processing unit, a second reference value using at least some of the data points in the histogram corresponding with a future phase value, and adding the difference and the second reference value to predict the future signal value; and providing, by the processing unit,
a control signal to a controller for controlling a component of a radiation system based at least in part on the future signal value that is predicted by the processing unit.

2. The method of claim 1, wherein at least one of the first reference value and the second reference value comprises an average value.

3. The method of claim 1, wherein at least one of the first reference value and the second reference value comprises a median value.

4. The method of claim 1, wherein the output is generated for indicating non-periodicity of a breathing of the subject.

5. The method of claim 1, wherein the signal value that is associated with a current respiratory cycle comprises a current signal value.

6. The method of claim 1, further comprising updating the signal-phase histogram by disregarding one or more of the signal values that are older than a prescribed period.

7. A method of processing breathing signals of a subject, comprising:
obtaining breathing signals of a subject using a breathing monitoring device;
determining a signal-phase histogram using the breathing signals, wherein the signal-phase histogram comprises a plurality of data points, each of the data points having at least a phase value and a signal value;
obtaining, by a processing unit, a current signal value that is associated with a current time instant in a respiratory cycle;
obtaining, by the processing unit, a future phase value;
predicting, by the processing unit, a future signal value, wherein the act of predicting the future signal value comprises determining a delta value representing a difference between the current signal value and a reference signal associated with the signal-phase histogram, and applying the delta value for the future phase value to predict the future signal value; and
providing a control signal to a controller for controlling a component of a radiation system based at least in part on the future signal value that is predicted by the processing unit.

8. The method of claim 7, further comprising updating the signal-phase histogram by disregarding one or more of the signal values that are older than a prescribed period.

9. The method of claim 7, wherein the component of the radiation system is controlled by using the predicted future signal value to control a delivery of treatment radiation.

10. The method of claim 7, wherein the component of the radiation system is controlled by using the predicted future signal value to control an imaging process.

11. A method of processing breathing signals of a subject, comprising:
obtaining breathing signals of a subject using a breathing monitoring device;
determining a signal-phase histogram using the breathing signals, wherein the signal-phase histogram comprises a plurality of data points, each of the data points having at least a phase value and a signal value;
obtaining a current signal value that is associated with a current time instant in a respiratory cycle;
obtaining a future phase value; and
predicting a future signal value using the current signal value, the future phase value, and the signal-phase histogram;
wherein the act of predicting the future signal value comprises:
determining, by a processing unit, a first reference value using at least some of the data points in the histogram that correspond with a current phase value;
determining, by the processing unit, a difference between the current signal value and the first reference value;
determining, by the processing unit, a second reference value using at least some of the data points in the histogram that correspond with the future phase value; and
adding, by the processing unit, the difference and the second reference value to determine the future signal value; and
providing, by the processing unit, a control signal to a controller to control a component of a radiation system based at least in part on the future signal value that is determined by the processing unit.

12. The method of claim 11, wherein at least one of the first reference value and the second reference value is determined by determining an average value using at least some of the data points in the signal-phase histogram.

13. The method of claim 11, wherein at least one of the first reference value and the second reference value is determined by determining a median value using at least some of the data points in the signal-phase histogram.

14. A system for processing breathing signals of a subject, comprising:
a processor configured for
obtaining breathing signals of a subject;
determining a signal-phase histogram using the breathing signals, wherein the signal-phase histogram comprises a plurality of data points, each of the data points having at least a phase value and a signal value;
obtaining a current signal value that is associated with a current time instant in a respiratory cycle; and
obtaining a future phase value; and
predicting a future signal value, wherein the processor is configured to predict the future signal value by determining a delta value representing a difference between the current signal value and a reference signal associated with the signal-phase histogram, and applying the delta value for the future phase value to predict the future signal value; and
providing a control signal to a controller to control a component of a radiation system based at least in part on the future signal value that is predicted by the processor.

15. A computer product having a set of instructions stored in a non-transitory medium, wherein an execution of the instructions causes a process to be performed, the process comprising:

obtaining breathing signals of a subject;
determining a signal-phase histogram using the breathing signals, wherein the signal-phase histogram comprises a plurality of data points, each of the data points having at least a phase value and a signal value;
obtaining, by a processing unit, a current signal value that is associated with a current time instant in a respiratory cycle;
obtaining, by the processing unit, a future phase value; and
predicting, by the processing unit, a future signal value, wherein the act of predicting the future signal value comprises determining a delta value representing a difference between the current signal value and a reference signal associated with the signal-phase histogram, and applying the delta value for the future phase value to predict the future signal value; and
providing, by the processing unit, a control signal to a controller to control a component of a radiation system based at least in part on the future signal value that is predicted by the processing unit.

* * * * *